United States Patent [19]

Takahashi et al.

[11] 4,168,203

[45] Sep. 18, 1979

[54] QUANTITATIVE ANALYSIS OF NEUTRAL LIPIDS AND LECITHIN

[75] Inventors: Ziuro Takahashi, Itami; Setsuko Hirano, Anryu; Akira Sawada, Takarazuka, all of Japan

[73] Assignee: Fujisawa Pharmaceutical Co., Ltd., Osaka, Japan

[21] Appl. No.: 573,178

[22] Filed: Apr. 30, 1975

[30] Foreign Application Priority Data

Apr. 30, 1974 [JP] Japan .................................. 49/48928

[51] Int. Cl.$^2$ ..................... C12K 1/00; G01N 31/14
[52] U.S. Cl. ..................................... 435/21; 435/19
[58] Field of Search .................. 195/103.5 R, 2, 3 R, 195/99

[56] References Cited

U.S. PATENT DOCUMENTS

| | | | |
|---|---|---|---|
| 3,703,591 | 11/1972 | Bucolo et al. | 195/103.5 R |
| 3,759,793 | 9/1973 | Stork et al. | 195/103.5 R |
| 3,862,009 | 1/1975 | Wahlefeld et al. | 195/103.5 R |

OTHER PUBLICATIONS

D. L. Horney, "An Approach to the Measurement of Total Lipid Glycerol in Serum" Clin. Chem. 19 (5), 453–458, (1973).

*Primary Examiner*—Raymond N. Jones
*Assistant Examiner*—Esther M. Kepplinger
*Attorney, Agent, or Firm*—Oblon, Fisher, Spivak, McClelland & Maier

[57] ABSTRACT

A reagent for quantitative analysis of neutral lipids in serum or internal organs comprising a lipase produced by the NRS-400 strain of Rhizopus and an aqueous solvent.

8 Claims, No Drawings

QUANTITATIVE ANALYSIS OF NEUTRAL LIPIDS AND LECITHIN

BACKGROUND OF THE INVENTION

1. Field of the Invention

The present invention relates to a reagent for quantitative analysis of neutral lipids and lecithin in serum or internal organs.

2. Description of the Prior Art

In the past, the determination of the content of neutral lipids and phospholipids, especially lecithin, in serum or internal organs has always included clinical examination of lipid metabolism or biological experiments and tests.

The conventional methods for carrying out these determinations have not been satisfying because they comprise a series of extremely complicated processes often requiring manual operations consisting of extraction, elimination of phospholipids, saponification and elimination of protein. For quantitative analysis of phospholipids such as lecithin, there has been generally adopted the so-called wet ash process which comprises treatment with a strong acid and an oxidizing agent at an elevated temperature. However, this process suffers from several serious disadvantages because it requires drastic conditions and troublesome operations as well as a long time for completion. Furthermore, the selective determination of lecithin is impossible using the conventional process. Consequently, it would be most desirable to have a quantitative technique for selective determination of lecithin content which is free from the disadvantages of the prior art processes.

SUMMARY OF THE INVENTION

Accordingly, it is one object of this invention to provide a reagent for quantitative analysis of neutral lipids and lecithin in serum or internal organs which makes it possible to selectively determine the content of lecithin in the phospholipids.

It is another object of this invention to enable the determination of the contents of neutral lipids and lecithin in serum or internal organs rapidly under mild conditions by a simple operation.

It is still another object of this invention to provide a technique for determination of the content of neutral lipids and lecithin employing automatic analysis using a flow system.

Briefly, these and other objects of this invention have been accomplished by providing a reagent for quantitative analysis which comprises a lipase produced by the NRS-400 strain of Rhizopus and an aqueous solvent; and a reagent for quantitative analysis of neutral lipids and lecithin in serum or internal organs which comprises a lipase having both a lipase activity and a lipoprotein lipase activity, a phospholipase C and an aqueous solvent.

DESCRIPTION OF THE PREFERRED EMBODIMENTS

It has been found in this invention that determination of the concentration of neutral lipids combined with proteins in serum and internal organs can be effected by treating the specimen with a commercially available lipase isolated from the NRS-400 strain of Rhizopus (trade name Lipase "Saiken" manufactured by Osaka Saikin Kenkyusho K.K.), having both a lipase activity and a lipoprotein lipase activity. This can be accomplished directly without separation of the lipids from the proteins prior to the determination since the neutral lipids combined with proteins are rapidly decomposed into glycerols. In addition, by combined use of a lipase having both a lipase activity and a lipoprotein lipase activity, such as Lipase "Saiken", and a phospholipase C, there can be determined not only the amount of neutral lipids, but also the lecithin content of a specimen of serum or an internal organ containing both neutral lipids and lecithin. This is possible since lecithin is converted by the phospholipase C into diglycerides, which are then converted into glycerols by the lipase having both a lipase activity and a lipoprotein lipase activity. The present invention is based on these findings.

By the use of the reagent of this invention, both the amount of neutral lipids (A) and the total amount of neutral lipids and lecithin (B) can be determined. The amount of lecithin can be then calculated by deducting the value (A) from the value (B). The determination of lecithin content by the reagent of this invention can also be performed directly when the specimen has been previously subjected to a conventional treatment for eliminating neutral lipids.

Suitable for use as the lipase having both a lipase activity and a lipoprotein lipase activity, there are included, for example, a lipase produced by the NRS-400 strain of Rhizopus and a lipase produced by Pseudomonas fluorescens. Any other lipase having both a lipase activity and a lipoprotein lipase activity may also be used.

Suitable for use as the phospholipase C are included any which can decompose lecithin into diglycerides.

The aqueous solvent should be one which can maintain the lipase produced by the NRS-400 strain of Rhizopus, the lipase having both a lipase activity and a lipoprotein lipase activity and the phospholipase C under a pH of 7 to 8, prefereably 7.5 to 7.7. Suitable solvents include water (distilled) and a buffer such as Tris-hydrochloric acid buffer, a phosphoric acid buffer or a boric acid buffer.

The reagent of this invention can be prepared by dissolving the lipase produced by the NRS-400 strain of Rhizopus, or the lipase having both a lipase activity and a lipoprotein lipase activity and the phospholipase C, into the aqueous solvent. In order to prevent a decrease in the activities of the enzymes, preparation upon each use is desirable.

The concentration of the lipase produced by the NRS-400 strain of Rhizopus in the reagent of the invention should be about 55,000 U/ml or more, preferably 80,000 U/ml, when the concentration of the neutral lipids in the serum or the internal organ is 1000 $\mu$M/dl or less. When the concentration of lecithin in the specimen is 1000 $\mu$M/dl or less, the concentration of the phospholipase C should be about 5 IU (International Unit)/ml or more, preferably 10 IU/ml, and the concentration of the lipase having both a lipase activity and a lipoprotein lipase activity should be about 55,000 U/ml or more, preferably 80,000 U/ml.

The reagent of the invention may also contain any suitable supplementary agent such as an enzyme-activating atent, e.g., $Ca^{++}$ or $Mg^{++}$ ions.

When the specimen is a serum, it can be directly subjected to the determination of neutral lipids or lecithin contents by the reagent of this invention without previous treatment. In the case of an internal organ, the organ is first homogenized by any conventional procedure and dispersed in an aqueous solvent prior to the determination of the amount of neutral lipids or lecithin.

The determination of neutral lipids content in the specimen may be effected by adding the reagent comprising the lipase produced by the NRS-400 strain of Rhizopus and the aqueous solvent to a predetermined amount of the specimen, warming the mixture to 30° to 40° C., preferably about 37° C., for about 20 to 40 minutes and then using any conventional procedure to measure the amount of the glycerols produced. For the determination of the neutral lipids and lecithin contents in the specimen, the reagent comprising the lipase which has both a lipase activity and a lipoprotein lipase activity, the phospholipase C and the aqueous solvent is added to the specimen, and the mixture is treated as above.

The determination of the amounts of neutral lipids and lecithin in the specimen may alternatively be affected by adding to the specimen the reagent comprising the phospholipase C and the aqueous solvent, then adding thereto the reagent comprising the lipase which has both a lipase activity and a lipoprotein lipase activity and the aqueous solvent and treating the mixture as above mentioned. (See Experiment 2 below).

The following experiments illustrate in detail the quantitative analytical procedure for determination of the amounts of neutral lipids and lecithin in serum by the use of the reagent of the invention. These experiments are not intended to be limiting in any way unless otherwise specified.

Experiment 1

A specimen of serum (50 μl) is charged into a test tube and warmed to 37° C. The reagent obtained in Example 1 (100 μl) below is added thereto. The mixture is maintained at 37° C. for 20 minutes. Then, the reagent for determination of the amount of glycerol (1) (0.3 ml) (defined below) is added thereto, and the mixture is kept at 37° C. for 20 minutes. To the resultant mixture, the reagent for determination of the amount of glycerol (2) (1 ml) (defined below) is added, and the mixture is allowed to stand at room temperature for 15 minutes. Then, the reagent for determination of the amount of glycerol (3) (5 ml) (defined below) is further added thereto, and, after 10 minutes, a colorimetric determination of glycerol is carried out at a wavelength of 450 mμm. The thus determined glycerols are considered to be derived from triglycerides. From the obtained value of the amount of the glycerols, the amount of the triglycerides is calculated.

For comparison, an equivalent specimen of serum as used above is subjected to the determination of neutral lipids content by the conventional acetylacetone method (adopting the periodate oxidation-acetylacetone coloring process using Triglykit (Eiken)).

The results are shown in the following table.

| Specimen No. | Acetylacetone method (mg/dl) | By use of reagent of Example 1 (mg/dl) |
|---|---|---|
| 1 | 129 | 122 |
| 2 | 300 | 288 |
| 3 | 168 | 190 |
| 4 | 148 | 146 |
| 5 | 95 | 98 |
| 6 | 246 | 233 |
| 7 | 179 | 188 |
| 8 | 126 | 126 |
| 9 | 154 | 135 |
| 10 | 185 | 198 |

-continued

| Specimen No. | Acetylacetone method (mg/dl) | By use of reagent of Example 1 (mg/dl) |
|---|---|---|
| 11 | 126 | 120 |
| 12 | 157 | 153 |
| 13 | 143 | 147 |
| 14 | 196 | 194 |
| 15 | 112 | 113 |
| 16 | 126 | 126 |
| 17 | 90 | 80 |
| 18 | 112 | 105 |
| 19 | 92 | 90 |
| 20 | 238 | 222 |
| 21 | 140 | 150 |
| 22 | 104 | 105 |
| 23 | 154 | 150 |
| 24 | 207 | 213 |
| 25 | 90 | 98 |
| 26 | 183 | 173 |
| 27 | 171 | 158 |
| 28 | 98 | 56 |
| 29 | 132 | 120 |
| 30 | 118 | 105 |

The average relative coefficient between the two determinations is 0.97.

Reagents for determination of the amount of glycerol:

(1): ATP (adenosine triphosphate; manufactured by Boeringer AG), PEP (phosphoenolpyruvic acid; manufactured by Boeringer AG), Glycerokinase (manufactured by Boeringer AG; 85 IU/mg, 5 mg/ml) and Pyruvic acidkinase (manufactured by Boeringer AG; 150 IU/mg, 2 mg/ml) are each dissolved in a 1/15 M phosphoric acid buffer containing magnesium chloride (5 mM) so as to be present in a concentration of 0.4 mg/ml, 4 mg/ml, 8.5 IU/ml and 1.2 IU/ml, respectively. The separate solutions are then mixed in identical amounts.

(2): 2,4-Dinitrophenylhydrazine is dissolved in 1 N hydrochloric acid to a concentration of 2 mM.

(3): A 0.6 N aqueous solution of sodium hydroxide is formed.

Experiment 2

Into each of two test tubes, there is charged a specimen of serum (50 μl). One of the tubes is subjected to the procedure of Experiment 1 to determine the amount of glycerols derived from triglycerides (A).

The other tube is subjected to the following procedure. The specimen is warmed to 37° C., and the solution containing phospholipase C (5 IU/ml) obtained in Example 5 (100 μl) is added thereto, and the mixture is allowed to stand for 20 minutes. The resultant mixture is then treated with the reagents for glycerol as in Experiment 1 to determine the amount of glycerols derived from both neutral lipids and lecithin in the serum (B).

By subtracting (A) from (B), the amount of the glycerols derived from lecithin alone is obtained. From this, the amount of lecithin is calculated.

The results are shown in the following table.

| Specimen No. | A (μM/dl) | B (μM/dl) | B − A (μM/dl) | Amount of lecithin mg/dl |
|---|---|---|---|---|
| 1 | 175 | 350 | 175 | 139 |
| 2 | 75 | 225 | 150 | 119 |
| 3 | 470 | 740 | 270 | 215 |
| 4 | 105 | 270 | 165 | 131 |
| 5 | 285 | 535 | 250 | 199 |

Having generally described the invention, a more complete understanding can be obtained by reference to certain specific examples, which are included for purposes of illustration only and are not intended to be limiting unless otherwise specified.

EXAMPLE 1

Lipase "Saiken" (manufactured by Osaka Saiken Kenkyusho K.K.; $800 \times 10^4$ U/g) (10 mg) and magnesium chloride (5 mM) are dissolved in a 1/15 M boric acid buffer solution (pH 7.7) (1 ml) to obtain a reagent with a concentration of 80,000 U/ml.

EXAMPLE 2

Lipase "Saiken" (manufactured by Osaka Saikin Kenkyusho K.K.; $800 \times 10^4$ U/g) (50 mg) and magnesium chloride (5 mM) are dissolved in a 1/15 M phosphoric acid buffer solution (pH 7.7) (5 ml) to obtain a reagent with a concentration of 80,000 U/ml.

EXAMPLE 3

Lipase "saiken" (manufactured by Osaka Saikin Kenkyusho K.K.; $800 \times 10^4$ U/g) (10 mg) is dissolved in a 1/15 M boric acid buffer solution (pH 7.7) (1 ml) to obtain a reagent with a concentration of 80,000 U/ml.

EXAMPLE 4

Lipase "saiken" (manufactured by Osaka Saikin Kenkyusho K.K.; $800 \times 10^4$ U/g) (50 mg) is dissolved in a 1/15 M phosphoric buffer solution (pH 7.7) (5 ml) to obtain a reagent with a concentration of 80,000 U/ml.

EXAMPLE 5

Phospholipase C (manufactured by Sigma Co., Ltd.; 5 IU/mg) (1 mg) and magnesium chloride (5 mM) are dissolved in a 1/15 M boric acid buffer solution (1 ml) and the resultant solution (5 IU/ml) is admixed with the solution obtained in Example 1 to prepare a reagent.

EXAMPLE 6

Phospholipase C (manufactured by Sigma Co., Ltd; 5 IU/mg) (5 mg) and magnesium chloride (5 mM) are dissolved in a phosphoric acid buffer solution (5 ml) and the resultant solution (5 IU/ml) is admixed with the solution obtained in Example 2 to prepare a reagent.

EXAMPLE 7

Phospholipase C (manufactured by Sigma Co., Ltd.; 5 IU/mg) (1 mg) is dissolved in a 1/15 M boric acid buffer solution (1 ml), and the resultant solution (5 IU/ml) is admixed with the solution obtained in Example 3 to prepare a reagent.

EXAMPLE 8

Phospholipase C (manufactured by Sigma Co., Ltd.; 5 IU/mg) (5 mg) is dissolved in a 1/15 M phosphoric acid buffer solution (5 ml), and the resultant solution (5 IU/ml) is admixed with the solution obtained in Example 4 to prepare a reagent.

EXAMPLE 9

Lipase "Saiken" (manufactured by Osaka Saikin Kenkyusho K.K.; $800 \times 10^4$ U/g) (10 mg) and Phospholipase C (manufactured by Sigma Co., Ltd.; 5 IU/mg) (1 mg) are dissolved in a 1/15 M boric acid buffer solution (1 ml) to obtain a reagent having a lipase concentration of 80,000 U/ml and a phospholipase C concentration of 5 IU/ml.

EXAMPLE 10

Lipase produced by the NRS-400 strain of Rhizopus (manufactured by Osaka Saikin Kenkyusho K.K.; $800 \times 10^4$ U/g) (50 mg) and a 1/15 M boric acid buffer solution (5 ml) containing magnesium chloride (5 mM) are mixed to obtain a reagent with a concentration of 80,000 U/ml.

EXAMPLE 11

Phospholipase C (manufactured by Sigma Co., Ltd.; 5 IU/mg) (5 mg) and magnesium chloride (5 mM) are dissolved in a phosphoric acid buffer solution (5 ml) to obtain a solution containing Phospholipase C in a concentration of 5 IU/ml.

Then, Lipase "Saiken" (manufactured by Osaka Saikin Kenkyusho K.K.; $800 \times 10^4$ U/g) (50 mg) and magnesium chloride (5 mM) are dissolved in a 1/15 M phosphoric acid buffer solution (pH 7.7) (5 ml) to obtain a solution containing the said lipase in a concentration of 80,000 U/ml. The two kinds of solutions thus obtained are mixed to prepare a reagent.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A reagent for quantitative analysis of neutral lipids in serum or internal organs which consists essentially of a lipase produced by the NRS-400 strain of Rhizopus and an aqueous solvent comprising water and a buffer selected from the group consisting of tris-hydrochloric acid buffer, phosphoric acid buffer and boric acid buffer which maintains the reagent at a pH of from 7 to 8.

2. The reagent of claim 1, wherein the concentration of the Rhizopus strain is more than 55,000 U/ml when the concentration of neutral lipids in the specimen is less than 1000 $\mu$M/dl.

3. A reagent for quantitative analysis of neutral lipids and lecithin in serum or internal organs which consists essentially of a lipase having both a lipase activity and lipoprotein activity, said lipase produced by the NRS-400 strain of Rhizopus, a phospholipase C and an aqueous solvent comprising water and a buffer selected from the group consisting of tris-hydrochloric acid buffer, phosphoric acid buffer and boric acid buffer which maintains the reagent at a pH of from 7 to 8.

4. The reagent of claim 3, wherein the concentration of the phospholipase C is more than 5 IU/ml and the concentration of the lipase is more than 55,000 U/ml when the concentration of lecithin in the specimen is less than 1000 $\mu$M/dl.

5. A method for quantitative determination of neutral lipids in a specimen selected from the group consisting of serum or internal organs which comprises adding the reagent of claim 1 to the specimen, warming the mixture to 30 to 40° C. for about 20 to 40 minutes and measuring the amount of glycerols produced.

6. A method for quantitative determination of neutral lipids and lecithin in a specimen selected from the group consisting of serum or internal organs which comprises adding the reagent of claim 3 to the specimen, warming the mixture to 30° to 40° C. for about 20 to 40 minutes and measuring the amount of glycerols produced.

7. A method for quantitative determination of lecithin in a specimen selected from the group consisting of serum or internal organs which consists of performing the method of claim 5 on a specimen to determine the amount of neutral lipids (A), performing the method of claim 6 on an equivalent specimen to determine the amount of neutral lipids and lecithin (B), and subtracting A from B to determine the amount of lecithin.

8. A method for direct quantitative determination of lecithin in a specimen selected from the group consisting of serum or internal organs which consists of carrying out the method of claim 6 on a specimen from which neutral lipids have been eliminated.

* * * * *